United States Patent
Liu et al.

(10) Patent No.: US 8,569,561 B2
(45) Date of Patent: Oct. 29, 2013

(54) METHOD FOR REVAMPING AN HF OR SULPHURIC ACID ALKYLATION UNIT

(75) Inventors: Zhichang Liu, Beijing (CN); Chunming Xu, Beijing (CN); Rui Zhang, Beijing (CN); Xianghai Meng, Beijing (CN); Ana Cecilia Patroni, Amsterdam (NL); Peter Anton August Klusener, Amsterdam (NL); Albertus Vincentius Petrus Van Den Bosch, Amsterdam (NL)

(73) Assignee: Shell Oil Company, Houston, TX (US)

( * ) Notice: Subject to any disclaimer, the term of this patent is extended or adjusted under 35 U.S.C. 154(b) by 113 days.

(21) Appl. No.: 13/388,563

(22) PCT Filed: Aug. 6, 2010

(86) PCT No.: PCT/EP2010/061515
§ 371 (c)(1),
(2), (4) Date: Mar. 13, 2012

(87) PCT Pub. No.: WO2011/015664
PCT Pub. Date: Feb. 10, 2011

(65) Prior Publication Data
US 2012/0159759 A1    Jun. 28, 2012

(30) Foreign Application Priority Data
Aug. 6, 2009    (WO) ............... PCT/CN2009/000886

(51) Int. Cl.
*C07C 2/60*    (2006.01)
*C07C 2/62*    (2006.01)

(52) U.S. Cl.
USPC ........... 585/709; 585/719; 585/723; 585/730; 585/899

(58) Field of Classification Search
USPC .......................... 585/709, 719, 723, 730, 899
See application file for complete search history.

(56) References Cited

U.S. PATENT DOCUMENTS

| | | | |
|---|---|---|---|
| 7,285,698 B2 | 10/2007 | Liu et al. | 585/721 |
| 2004/0133056 A1 | 7/2004 | Liu et al. | 585/721 |

FOREIGN PATENT DOCUMENTS

GB    647155    12/1950

*Primary Examiner* — Thuan D Dang
(74) *Attorney, Agent, or Firm* — Charles W. Stewart

(57) ABSTRACT

The present invention provides a method for revamping an HF or sulphuric acid alkylation unit to an ionic liquid alkylation unit, wherein the HF or sulphuric acid alkylation unit comprise at least: —a reactor unit for contacting catalyst and hydrocarbon reactants; —a separator unit for separating a reactor effluent into a catalyst phase and an alkylate-comprising hydrocarbon phase; —a fractionator unit for fractionating the alkylate-comprising hydrocarbon phase into at least one stream comprising alkylate; and which method includes: —providing one or more cyclone units downstream of the reactor unit to separate at least part of the reactor effluent in a catalyst phase and a alkylate-comprising hydrocarbon phase.

5 Claims, 2 Drawing Sheets

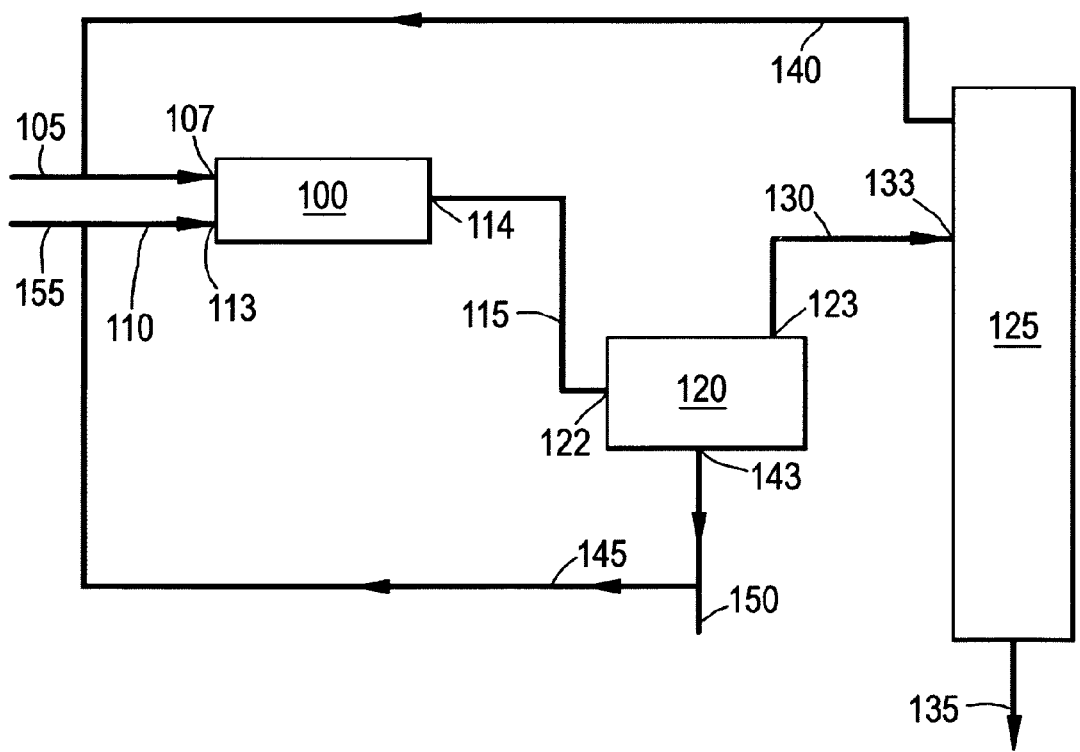

METHOD FOR REVAMPING AN HF OR SULPHURIC ACID ALKYLATION UNIT

PRIORITY CLAIM

Figure 2A:
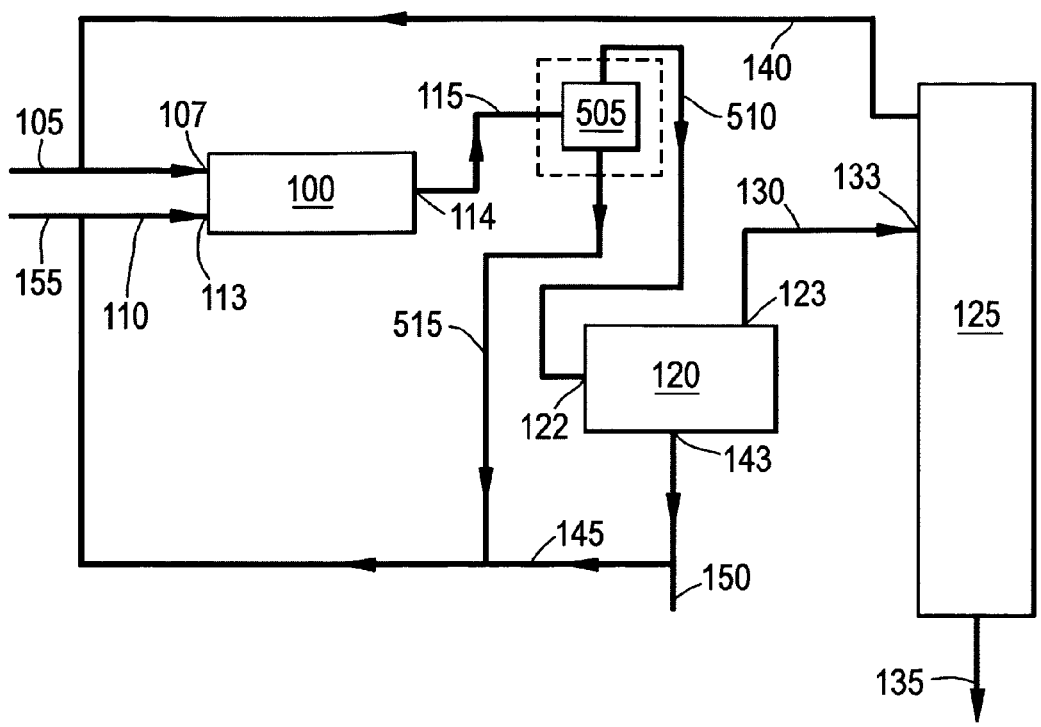

The present application claims priority from PCT/EP2010/061515, filed 6 Aug. 2010, which claims priority from PCT/CN2009/000886, filed 6 Aug. 2009.

The present invention provides a method for revamping an HF or sulphuric acid alkylation unit.

There is an increasing demand for alkylate fuel blending feedstock. As a fuel-blending component alkylate combines a low vapour pressure, no olefin or aromatic content with high octane properties.

Almost all alkylate is produced by reacting isobutane with butene in the presence of a suitable acidic catalyst. The most used catalysts are HF (hydrofluoric acid) and sulphuric acid. Although well established, these processes suffer numerous disadvantages. In case of HF, stringent health and safety measures must be applied requiring significant investments. In case of sulphuric acid, the large consumption of catalyst and the need to provide utilities for refrigeration are unfavourable from an economic standpoint.

Recently, the alkylation of isoparaffins with olefins using an ionic liquid catalyst has attracted attention as an alternative to HF and sulphuric acid catalysed alkylation processes.

In for instance U.S. Pat. No. 7,285,698 a process for manufacturing an alkylate oil is disclosed, which uses a composite ionic liquid catalyst to react isobutane with a butene. In the process of U.S. Pat. No. 7,285,698, isobutane and butene are supplied to a reactor unit and the alkylate is formed by contacting the reactants with a composite ionic liquid under alkylation conditions. The reactor effluent is separated into a hydrocarbon phase and an ionic liquid phase. The ionic liquid phase is recycled to the reactor unit while the hydrocarbon phase is treated to retrieve the alkylate.

Current alkylation units have been specifically designed for either HF or sulphuric acid (also referred to as SA) catalyst and are not optimally suited for use of a different catalyst such as an ionic liquid (also referred to as IL) catalyst. In for instance Liu et al. (Z. Liu, R. Zhang, C. Xu, R. Xia, Ionic liquid alkylation process produces high-quality gasoline, Oil and Gas Journal, vol 104, Issue 40, 2006) it is mentioned that it is possible to retrofit a sulphuric acid alkylation unit for use of an IL catalyst. In Liu et al., it proposed to add a surge tank for IL recycle and to modify the settler internals to enhance separation of the IL. However, it was found by Liu that the performance of the retrofitted alkylation unit was less than optimal.

Therefore, there is a need in the art for an improved method for revamping HF or SA alkylation unit to an IL alkylation unit.

It has now been found that the performance of an HF or SA alkylation unit, which was revamped for use as an IL alkylation unit may be improved by modifying the existing alkylation unit.

It has also been found that the less than optimal results reported by Liu et al, are at least in part caused incomplete separation of the hydrocarbon phase and the catalyst phase in the separator unit, i.e. the settler unit.

Due to the different properties of an IL catalyst compared to SA or HF the separation of an IL catalyst from a hydrocarbon phase is different from the separation of either SA or HF from a hydrocarbon phase. As a consequence, the settler design of the HF or SA alkylation unit may not provide sufficient separation capacity for separation the hydrocarbon and catalyst phases. As a result catalyst remains in the hydrocarbon phase and vice versa. As a result, catalyst consumption increases and additionally, the hydrocarbon phase is contaminated with catalyst. In addition, the hydrocarbon recycle volumes may increase due to the higher isoparaffin to olefin molar ratios used in an IL alkylation process. In a typical HF and SA alkylation processes, the isoparaffin to olefin molar ratios used is in the range of 1 to 10. For an IL alkylation process the isoparaffin to olefin molar ratios used are preferably above 20 or even above 100.

Therefore the present invention also provides a method for revamping an HF or sulphuric acid alkylation unit to an ionic liquid alkylation unit, wherein the HF or sulphuric acid alkylation unit comprise at least:

a reactor unit for contacting catalyst and hydrocarbon reactants;

a separator unit for separating a reactor effluent into a catalyst phase and an alkylate-comprising hydrocarbon phase;

a fractionator unit for fractionating the alkylate-comprising hydrocarbon phase into at least one stream comprising alkylate; and which method includes:

providing one or more cyclone units downstream of the reactor unit to separate at least part of the reactor effluent in a catalyst phase and a alkylate-comprising hydrocarbon phase.

The present invention relates to a method for revamping an HF or SA alkylation unit to an IL alkylation unit. Reference herein to revamping is to modifying or adapting an existing unit or process line-up designed for operating a specific process, such that it is suitable for operating another process. The obtained IL alkylation unit is used to produce alkylate by reacting an isoparaffin with an olefin in the presence of an IL catalyst under alkylation conditions. Typical IL alkylation conditions (or process conditions) are known in the art, whereby it will be appreciated that actual operational process conditions are among others dependent of the exact composition of the reactants and catalyst.

The temperature in the reactor unit is preferably in the range of from −20 to 100° C., more preferably in the range of from 0 to 50° C., however the temperature must be high enough to ensure that the ionic liquid is in its liquid form.

To suppress vapour formation in the reactor, the process is performed under pressure, preferably the pressure in the reactor is in the range of from 0.1 to 1.6 MPa.

The alkylation process may be a semi-continues or continuous process. Typically, the isoparaffin is an isobutane or an isopentane and the olefin is an olefin comprising in the range of from 2 to 8 carbon atoms, more preferably of from 3 to 6 carbon atoms, even more preferably 4 or 5 carbon atoms. Examples of suitable olefins include, propene, 1-butene, 2-butene, isobutene, 1-pentene, 2-pentene, 2-methyl-1-butene, 3-methyl-1-butene, 2-methyl-2-butene.

In an IL alkylation process, fresh isoparaffins and olefins are supplied to the process in a molar ratio, which is preferably 1 or higher, and typically in the range of from 1:1 to 40:1, more preferably 1:1 to 20:1. In the case of continuous reaction, the excess isoparaffin can be recycled to the reactor unit by recycling one or more isoparaffin-comprising streams.

Reference herein below to downstream is to the direction of the fluid flow path from the reactor unit to the fractionator unit. Reference herein upstream is to the opposite direction, i.e. from the fractionator unit to the reactor unit.

Existing HF and SA alkylation units comprise at least a reactor unit for contacting the reactants with the catalyst. The reactor unit preferably comprises at least one reactant inlet and at least one reactor effluent outlet. Preferably, the reactor unit also comprises at least one catalyst inlet. A typical reactor unit provided in sulphuric alkylation unit is a so-called Stratco contactor. In e.g. a Stratco contactor, the hydrocarbon reactants are introduced into an U-shaped reactor fluid flow path together with the catalyst. For HF alkylation typical reactors include e.g. Stratco contactors, gravity circulation reactors and emulsion reactors.

Generally, cooling tubes are provided in the reactor fluid flow path to remove the heat generated by the exothermic alkylation reaction. Alternatively, cooling is applied to the acid recycle stream. The effluent of the reactor unit is a mixture of catalyst and a hydrocarbon phase, the latter comprising an alkylate and unreacted reactants, predominantly isoparaffin.

The effluent of the reactor unit is normally provided to a separator unit to separate the reactor effluent into a catalyst phase and an alkylate-comprising hydrocarbon phase. Preferably, the separator unit comprises at least one inlet, typically for the reactor effluent or a stream generated there from, and at least one catalyst phase outlet and at least one alkylate-comprising hydrocarbon phase outlet.

The separator unit serves to separate the effluent of the reactor unit into an alkylate-comprising hydrocarbon phase and a catalyst phase. Preferably, the separator unit used in the HF and SA alkylation units to be revamped is a settler unit. Due to the low affinity of the HF and SA catalyst for hydrocarbons, the two phases separate readily under the influence of gravity. Reference herein to a settler unit is to any separator unit that separates two liquid phases under the influence of gravity. Actually, HF, SA and IL catalysts all have a density, which is higher than that of the hydrocarbon phase, therefore the reactor effluent is typically separated in the settler in an upper hydrocarbon phase and a lower catalyst phase.

In case of SA alkylation, catalyst phase recycle means are provided to recycle SA catalyst from the settler unit to the reactor unit. Typically, to maintain catalyst activity, part of the SA catalyst is removed from the process as spent catalyst and fresh SA catalyst is added to keep catalyst levels and activity intact.

In case of HF alkylation, the HF catalyst is regenerated and recycled to the process for reuse. For this reason, an HF alkylation unit comprises catalyst phase recycle means to recycle the HF catalyst, combined a separate regeneration.

In both SA as HF alkylation, the alkylate-comprising hydrocarbon phase, which was obtained in the settler is, at least in part, provided to a fractionator unit to obtain the retrieve the alkylate. The fractionator unit preferably comprises at least one alkylate-comprising hydrocarbon phase inlet. The fractionator unit, typically, comprises one or more distillation sub-units, including for instance a main fractionator (also referred to in the art as iso-stripper), an acid stripper and/or a depropaniser.

Following the fractionation, the obtained alkylate may be used to prepare avgas or as a blending component for gasoline. The hydrocarbon phase may also comprise significant amounts of unreacted isoparaffin. Preferably, such isoparaffin is at least partly recycled back to the reactor unit, via a provided means for recycling isoparaffin from the fractionator unit to the reactor. Other hydrocarbon streams may also be obtained by fractionation of the hydrocarbon phase, such a n-paraffin-comprising stream.

In existing HF or SA alkylation units means are provided to allow the reactants and catalyst to enter the reactor and to provide the reactor effluent to the separator unit and subsequently the alkylate-comprising hydrocarbon phase to the fractionator unit. It is not necessary to pass the reactor effluent directly from the reactor unit to the separator unit. The reactor effluent may undergo intermediate treatment such as cooling or heating in a heat exchanger. The same applies for the alkylate-comprising hydrocarbon phase being provided to the fractionator unit. Typically, a fluid flow fluid flow path for the reactants, products and catalyst is created by providing means to introduce reactants and catalyst to the reactor unit. In addition, means are provided to provide reactor effluent from the reactor effluent outlet of the reactor unit to the reactor effluent inlet of a separator unit located downstream from the reactor unit in the fluid flow path. Also, means are provided to provide an alkylate-comprising hydrocarbon phase from the alkylate-comprising hydrocarbon phase outlet of the separator unit to the alkylate-comprising hydrocarbon phase inlet of a fractionator unit located downstream from the separator unit in the fluid flow path and catalyst phase recycle means are provided to recycle catalyst from the settler unit to the reactor unit.

Ionic liquids are known in the art for their ability to catalyse alkylation reactions. The catalyst used in the present invention is a composite ionic liquid comprising cations derived from a hydrohalide of an alkyl-containing amine, imidazolium or pyridine. Preferably, the cations comprise nitrogen atoms, which are saturated with four substituents, among which there is at least one hydrogen atom and one alkyl group. More preferably, the alkyl substituent is at least one selected from methyl, ethyl, propyl, butyl, amyl, and hexyl groups. Examples of suitable cations include triethyl-ammonium ($NEt_3H^+$) and methyl-diethyl-ammonium cations ($MeNEt_2H^+$) or

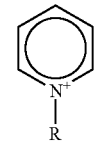

The anions of the composite ionic liquid are preferably aluminium based Lewis acids, in particular aluminium halides, preferably aluminium (III) chloride. Due the high acidity of the aluminium chloride Lewis acid it is preferred to combine the aluminium chloride, or other aluminium halide, with a second or more metal halide, sulphate or nitrate to form a coordinate anion, in particular a coordinate anion derived from two or more metal halides, wherein at least one metal halide is an aluminium halide. Suitable further metal halides, sulphates or nitrates, may be selected from halides, sulphates or nitrates of metals selected from the group consisting of Group IB elements of the Periodic Table, Group IIB elements of the Periodic Table and transition elements of the Periodic Table. Examples or suitable metals include copper, iron, zinc, nickel, cobalt, molybdenum, or platinum. Preferably, the metal halides, sulphates or nitrates, are metal halides, more preferably chlorides or bromides, such as copper (I) chloride, copper (II) chloride, nickel (II) chloride, iron (II) chloride. Preferably, the molar ratio of the aluminium compound to the other metal compounds in the range of from 1:100-100:1, more preferably of from 1:1-100:1, or even more preferably of from 2:1-30:1. By using a coordinate anion comprising aluminium and another metal, an improved alkylate product may be obtained. A method for preparing such catalyst is for instance described in U.S. Pat. No. 7,285,698. Particularly preferred catalysts are acidic ionic liquid catalysts comprising a coordinate anion derived from aluminium(III) chloride and copper(II) chloride or aluminium(III) chloride and copper(I) chloride.

In the method according to the present invention cyclones are provided to separate the reactor effluent. In current HF or SA alkylation units, settler units are provided to separate the HF or SA catalyst and the hydrocarbon phase from the reactor effluent. Using the existing settlers, designed to separate HF or SA from hydrocarbons, for separating IL catalyst and the alkylate-comprising hydrocarbon phase from the reactor effluent after the HF or SA alkylation unit has been revamped to and IL alkylation unit may result in several undesired effects, including:

- large settler volumes and undesirable large inventories of liquefied light hydrocarbons hydrocarbons due to high hydrocarbon recycle;
- carry over of catalyst to downstream hydrocarbon treating equipment;
- contamination of alkylate-comprising hydrocarbon phase, resulting in off-spec products;
- formation of hydrocarbon-catalyst emulsions in the settler, resulting in operational problems for settler level control;
- decreased catalyst rejuvenation regeneration effectiveness, both in terms of capital cost (larger equipment) and effectiveness of catalyst activity recovery due to the inclusion of a larger fraction of alkylate-comprising hydrocarbon phase in the catalyst.

Therefore, in the method according to the invention HF or SA alkylation unit to be revamped preferably comprises as the separator unit, a settler unit. In the method according to the present invention a cyclone unit is provided downstream of the reactor unit and means are provided to provide at least part of the reactor effluent to the cyclone unit to enhance separation of the catalyst phase and hydrocarbon phase. Using a cyclone unit it is possible to separate the reactor effluent into a lower density effluent comprising predominantly an alkylate-comprising hydrocarbon phase and a higher density effluent predominantly comprising an acidic ionic liquid catalyst phase. The cyclone unit may comprise one or more cyclone sub-units in series. Preferably, the cyclone unit comprises one or more hydro-cyclones. Reference herein to a hydro-cyclone is to a cyclone designed for the separation of water-hydrocarbon mixtures. More preferably, the cyclone unit comprises two or more cyclones or hydro-cyclones in series, wherein the low density predominantly alkylate-comprising hydrocarbon phase effluent of the first (hydro-)cyclone is provided to the next (hydro-)cyclone. This allows a further enhancement of the separation between the IL catalyst phase and the hydrocarbon phase. Preferably, the one or more cyclone units are provided in addition to the existing settler unit. Preferably, the one or more cyclone units are provided upstream of the settler unit and means are provided to pass the lower density, predominantly alkylate-comprising hydrocarbon phase effluent from the cyclone unit to the settler unit. By combining one or cyclones with one or more settlers located downstream from at least one of the cyclones, the ionic liquid fraction in lower density, predominantly alkylate-comprising hydrocarbon phase effluent may be lowered even further by subjecting the lower density, predominantly alkylate-comprising hydrocarbon phase effluent to a further physical separation treatment. Although, a settler unit may be relatively large in volume compared to e.g. a cyclone, if a settler unit is used downstream of a cyclone unit, the invention still provides an advantage as the settler unit will be much smaller than a settler unit in a conventional process, which is used to separate the reactor effluent.

The higher density effluent of the cyclone unit, which comprises predominantly catalyst phase, can be recycled to the reactor unit, optionally after being combined with catalyst phase obtained in the settler unit, if present. Optionally, two or more cyclones units can be applied in parallel to increase the capacity. These parallel cyclones units can be combined in series with one or more settlers.

In FIG. 1, a hydrocarbon mixture, comprising olefin and isoparaffin is provided to reactor unit 100, e.g. a Stratco contactor, via conduit (e.g. a pipe) 105, through reactant inlet 107. Catalyst, SA or IL, is also provided to reactor unit 100 through conduit 110 and catalyst inlet 113. In reactor unit 100, the hydrocarbon mixture and catalyst are contacted under alkylation conditions. Through reactor effluent outlet 114, a reactor effluent comprising catalyst and hydrocarbons is withdrawn from reactor unit 100 and supplied via conduit 115 to settler unit 120 through reactor effluent inlet 122. In settler unit 120, an alkylate-comprising hydrocarbon phase and a catalyst phase separate under influence of gravity. The hydrocarbon phase is withdrawn from separator unit 120 via alkylate-comprising hydrocarbon phase outlet 123 and provided to fractionator unit 125 through conduit 130 and alkylate-comprising hydrocarbon phase inlet 133. From the bottom of fractionator unit 125, an alkylate-comprising product is retrieved through conduit 135. The alkylate product can for instance be used for fuel blending purposes. Additionally, an isoparaffin product is retrieved from fractionator unit 125, which is recycled via conduit 140 to become part of the hydrocarbon mixture in conduit 105. Other hydrocarbon-comprising streams (not shown) may also be retrieved from fractionator 125.

The catalyst phase is withdrawn from separator unit 120 through catalyst phase outlet 143 and can be recycled via catalyst phase recycle conduit 145 to reactor unit 100. A spent catalyst fraction may be withdrawn from the process via conduit 150. Additional fresh catalyst can be provided to reactor unit 100 via conduit 155

Figure 2B:
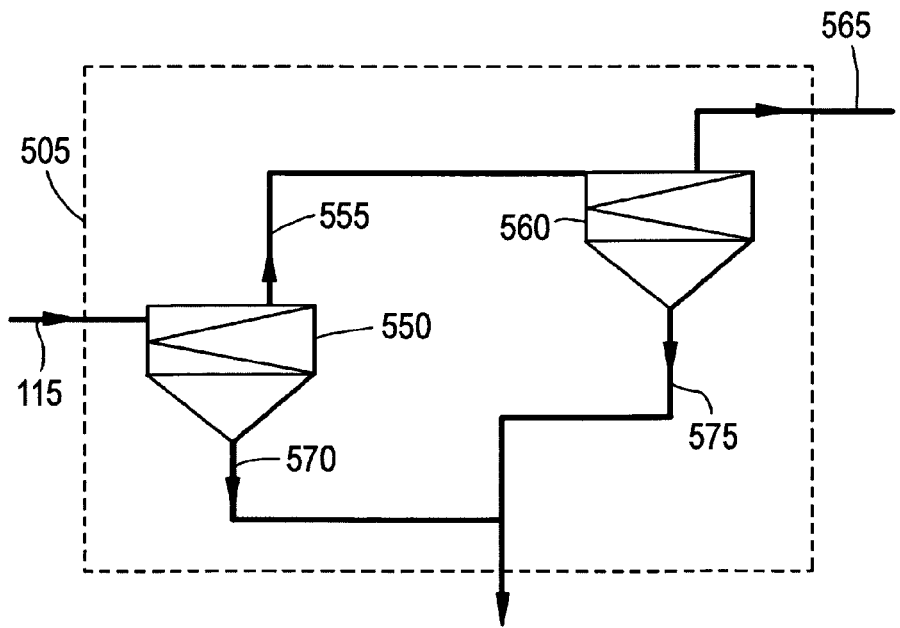

In FIG. 2A, a schematic representation is given of a SA alkylation unit as described in FIG. 1, which was revamped using the method according to the invention, wherein a cyclone unit is provided between the reactor unit and separator unit. In FIG. 2A, the reactor effluent is provided via conduit 115 to cyclone unit 505. The lower density, predominantly alkylate-comprising hydrocarbon, phase from the cyclone unit is provided to settler unit 120 via conduit 510. The higher density, predominantly catalyst, phase is provided to catalyst recycle conduit 145 via conduit 515. A more detailed representation of a possible cyclone unit 505 is given in FIG. 2B, wherein reactor effluent enters first cyclone sub-unit 550 in cyclone unit 505 via conduit 115. The lower density phase exits first cyclone sub-unit 550 via conduit 555 and is provided to second cyclone sub-unit 560 for further separation of catalyst phase from the alkylate-comprising hydrocarbon phase. A lower density alkylate-comprising hydrocarbon phase exits second cyclone sub-unit 560 via conduit 565 and is provided to settler unit 120. A higher density catalyst phase is obtained from both first cyclone sub-unit 550 and second cyclone sub-unit 560 via respectively conduit 570 and 575 and may be provided to catalyst recycle conduit 145.

Where FIGS. 1 to 2 refer to a SA alkylation unit, it will be appreciated that the same drawings could be used to represent an HF alkylation unit.

EXAMPLES

The invention is illustrated by the following non-limiting examples.

Example 1

In order to show the effectiveness of using a cyclone to separate the reactor effluent rather than a conventional settler, a sample reactor effluent, comprising a mixture of hydrocarbon reactants and products and ionic liquid catalyst was separated using a cyclone.

The sample reactor effluent comprises hydrocarbons and ionic liquid catalyst in a volume ratio of 1:1.05.

The operating temperature was maintained between 30 and 50° C. and the operating pressure was maintained between 0.1 to 0.5 MPa. The maximum feed rate of sample reactor effluent to the cyclone was 2 m$^3$/hr.

In a first run, 40 vol % of the sample reactor effluent was retrieved as lower density, predominantly alkylate-comprising hydrocarbon, phase.

The remaining 60 vol % of the sample reactor effluent was retrieved as higher density, predominantly catalyst, phase.

The lower density, predominantly alkylate-comprising hydrocarbon, phase comprised:
 95.5 vol % of hydrocarbons; and
 4.5 vol % of ionic liquid,
based on the volume of the lower density, predominantly alkylate-comprising hydrocarbon, phase.

The higher density, predominantly catalyst, phase comprised:
 17.7 vol % of hydrocarbons; and
 82.3 vol % of ionic liquid,
based on the volume of the higher density, predominantly catalyst, phase.

Using one separator approximately 79 vol % of the hydrocarbons originally provided in the sample reactor effluent were recovered in the lower density, predominantly alkylate-comprising hydrocarbon, phase.

In case the lower density, predominantly alkylate-comprising hydrocarbon, phase is further treated in a upstream settler unit, the size of volume of the settler unit is only 40% of a settler unit used to separate the whole reactor effluent.

In a second run, the sample reactor effluent was separated into a lower density, predominantly alkylate-comprising hydrocarbon, phase and a higher density, predominantly catalyst, phase using two separation steps. The obtained separation results are below.

50 vol % of the feed. i.e. sample reactor effluent, to the centrifuge was retrieved as a, lower density, intermediate phase and the remaining 50 vol % as higher density ionic liquid phase effluent.

The intermediate phase comprised:
 93.8 vol % of hydrocarbons; and
 6.2 vol % of ionic liquid,
based on the volume of the intermediate phase.

The higher density, predominantly catalyst, phase comprised:
 90.0 vol % of hydrocarbons; and
 10.0 vol % of ionic liquid,
based on the volume of the higher density, predominantly catalyst, phase.

The obtained intermediate phase was retrieved as an intermediate product and subjected to a second cyclone separation step. During the second cyclone separation step, 85 vol % of the intermediate phase was retrieved from the cyclone as, lighter density, hydrocarbon phase effluent and the remaining 15 vol % of the intermediate phase was retrieved as a higher density phase effluent, also referred to a (an)other effluent.

The lower density, predominantly alkylate-comprising hydrocarbon, phase comprised:
 98.5 vol % of hydrocarbons; and
 1.5 vol % of ionic liquid,
based on the volume of the lower density, predominantly alkylate-comprising hydrocarbon, phase.

The other effluent comprised:
 68.7 vol % of hydrocarbons; and
 31.3 vol % of ionic liquid,
based on the volume of the other effluent.

Using two separators approximately 86 vol % of the hydrocarbons originally provided in the sample reactor effluent were recovered in the lower density, predominantly alkylate-comprising hydrocarbon, phase.

By using two separators, in this case cyclones, in series to separate the lower density, predominantly alkylate-comprising hydrocarbon, phase from the sample reactor effluent, an increased fraction of the hydrocarbons in the sample reactor effluent can be retrieved and sent to the fractionator. This is due to the fact that a larger fraction of the reactor effluent is obtained as the intermediate phase from the first separator. Although, passing a larger fraction of the sample reactor effluent to the lighter intermediate phase causes the ionic liquid fraction in this multiple phase effluent to increase, the final ionic liquid fraction in the resulting lower density, predominantly alkylate-comprising hydrocarbon, phase is much lower due to the second separator step. As a result a larger fraction of the hydrocarbons in the reactor effluent can be separated from the ionic liquid. Using only one separator, the lower density, predominantly alkylate-comprising hydrocarbon, phase comprises only 79 vol % of the hydrocarbons originally present in the reactor effluent. In Example 1b, however, 86 vol % of the hydrocarbons in the reactor effluent were retrieved in the hydrocarbon effluent, comprising less ionic liquid.

In addition, the higher density, predominantly catalyst, phase comprised less hydrocarbons compared using only one separator, even in the case it is combined with the (an)other effluent.

In case the lower density, predominantly alkylate-comprising hydrocarbon, phase is further treated in a upstream settler unit, the size of volume of the settler unit is only 42.5% of a settler unit used to separate the whole reactor effluent.

What is claimed is:

1. A method for revamping an HF or sulphuric acid alkylation unit to an ionic liquid alkylation unit, wherein the HF or sulphuric acid alkylation unit comprises at least:
 a reactor unit for contacting catalyst and hydrocarbon reactants;
 a separator unit for separating a reactor effluent into a catalyst phase and an alkylate-comprising hydrocarbon phase;
 a fractionator unit for fractionating the alkylate-comprising hydrocarbon phase into at least one stream comprising alkylate; and
which method includes:
 providing one or more cyclone units downstream of the reactor unit to separate at least part of the reactor effluent in a catalyst phase and a alkylate-comprising hydrocarbon phase.

2. A method according to claim 1, wherein the one or more cyclone units are located upstream of the separator unit.

3. A method according to claim 1, wherein the separator unit is replaced by the one or more cyclone units.

4. A method according to claim 3, wherein cyclone unit comprises one or more cyclone sub-units in series.

5. A method according to claim 4, wherein the cyclone unit comprises one or more hydro-cyclones.

* * * * *